US008391962B2

(12) United States Patent
Watanabe

(10) Patent No.: US 8,391,962 B2
(45) Date of Patent: Mar. 5, 2013

(54) CARDIAC FUNCTION CIRCADIAN VARIATION ANALYSIS SYSTEM AND METHOD

(76) Inventor: Mari Alford Watanabe, University City, MO (US)

( * ) Notice: Subject to any disclaimer, the term of this patent is extended or adjusted under 35 U.S.C. 154(b) by 687 days.

(21) Appl. No.: 12/454,242

(22) Filed: May 13, 2009

(65) Prior Publication Data

US 2010/0292597 A1    Nov. 18, 2010

(51) Int. Cl.
*A61B 5/04* (2006.01)
(52) U.S. Cl. ........ 600/509; 600/508; 600/510; 600/515; 600/516; 600/517; 600/518; 600/519; 600/520; 600/521
(58) Field of Classification Search .......... 600/508–510, 600/515–521
See application file for complete search history.

(56) References Cited

U.S. PATENT DOCUMENTS 7,123,953 B2 * 10/2006 Starobin et al. ............... 600/516

* cited by examiner

*Primary Examiner* — Niketa Patel
*Assistant Examiner* — Mallika D Fairchild
(74) *Attorney, Agent, or Firm* — Daniel Klotzer; Klotzer Patents

(57) ABSTRACT

Systems and Methods for stratifying relative risks of adverse cardiac events by processing a duration of electrocardiograph recordings generally recorded by a Holter type of device. The duration of electrocardiograph recordings are processed to resolve RR interval related data, QT interval related data, and are fitted to formulas to at least partially establish fitting related measures. The fitting formulas incorporate circadian related periodic factors, and can further incorporate additional processing including utilizing Lissajous analysis techniques, among others.

13 Claims, 2 Drawing Sheets

CARDIAC FUNCTION CIRCADIAN VARIATION ANALYSIS SYSTEM AND METHOD

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

1. Field of the Invention

The present invention relates generally to systems and methods of identifying circadian rhythm related variations of human medical attributes, and more specifically to utilizing Lissajous analysis techniques for identifying cardiac function attributes that present circadian variations, and further utilizing the identified cardiac function attributes to forecast relative risks of sudden cardiac death (SCD).

2. Related Art

Among the more vexing issues still confronting medical professionals attempting to treat people with cardiac health issues, despite a number of substantial advances in both their diagnosis as well as their treatment, are difficulties in predicting exactly which patients are most susceptible to certain catastrophic negative outcomes, such as sudden cardiac death. Almost half a million people die in the U.S.A. suddenly each year from lethal electric rhythms of the heart, and many of these deaths could be prevented by surgically implanted defibrillators, if high risk patients can be accurately identified in advance. In the USA alone, tens of thousands of cardiac defibrillators are surgically implanted annually to prevent sudden cardiac death, but as many as 90% of them are unnecessary. Inadequate knowledge about what specific patient characteristics presage sudden cardiac death has led to establishment of a low threshold criterion for defibrillator implantation, namely, a left ventricular ejection fraction <30%. Per patient costs for initial implantation are $29,000~$55,000, which would result in an estimated annual cost of $5 billion if all American patients with ejection fraction <30% were to receive a defibrillator. To save one life using this criterion, it would reportedly be necessary to treat 11 patients, so that 10 out of 11 patients would receive defibrillators that would never be deployed, or worse, would not save their lives in spite of the pain, risk, and cost of the implantation. Currently, relatively crude heart pump function criterion are used to make most defibrillator implantation decisions, and it would be advantageous to determine electrically-based heart measurement characteristics capable of enhancing the heart pump function criteria when making these decisions. Better criteria would reduce health care costs as well as the physical and psychological burden borne by patients who unnecessarily receive defibrillators based on the current criterion. One of the more effective modern approaches to averting SCD in patients involves the implantation of cardiac defibrillators. The implanted defibrillators are relatively effective in averting the most negative consequences when a patient's heart fibrillates, but they are not without costs and drawbacks because their implanting involves major surgery with its attendant risks, discomforts, and expenses. Additionally, hereto now, it has not been possible to target those in critical need more accurately than the aforementioned one in ten. This inefficiency is because cardiologists have only crude criteria for predicting which patients' hearts are likely to fibrillate.

The crux of the issue, then, is the need for a reliable, accurate stratifier of patients' risk of SCD. The investigation of heart function manifestations represented in electrocardiograph recordings has provided substantial insights into the functioning of the human heart. The electrocardiographic QT interval (denoted herein as QT) has a long history of study as a risk stratifier, because physicians recognized early on that a long QT predisposes patients to potentially lethal rhythms of the heart called ventricular tachycardia, especially torsade de pointes. QT is also known to increase before the onset of ventricular tachyarrhythmias during acute myocardial ischemia. However, unlike most electrocardiographic measures with clear numerical limits on what is considered normal, QT has a nonlinear dependence on heart rate, and the raw QT by itself cannot be classified as being longer or shorter than normal, without accompanying heart rate information; additionally, besides its value depending on heart rate, the QT is also affected by cardiac sympathetic and vagal nerve activity. QT has also been examined as a possible predictor of ventricular fibrillation, but so far, predictions of SCD based on conventional QT characterizations, such as its reduction to a single value using heart rate correction formulas, have failed to dramatically reduce this inefficiency. The slope of QT plotted against the electrocardiographic RR interval (denoted herein as RR; essentially equivalent to the inverse of heart rate) has been found to be strongly correlated with fibrillation in animal and theoretical studies, which has led to recent studies investigating this slope for risk prediction value in humans.

Bazett's formula, first published in 1920, takes a QT and the prevailing heart rate, and produces a single value called rate-corrected QT interval (QTc). Therefore, QTc was one of the earliest QT based risk predictors studied. Despite some compelling evidence that long QTc after myocardial infarction [Schwartz 1978; Ahnve 1984] or in chronic ischemic heart disease [Puddu 1986] predicts SCD, large prospectively designed studies in patients surviving myocardial infarction [Pohjola-Sintonen 1986, Wheelan 1986] and the Framingham Heart Study [Goldberg 1991] have failed to verify the utility of QTc as a risk predictor. The focus of QT based studies then shifted to other measures of QT, such as 24 hour QT variability [Homs 1997], QT dispersion [Molnar 1997], and day-night difference in QT [Yi 1998]. The study of these parameters helped to advance knowledge about QT dynamics, but yielded little with respect to risk prediction. More recently, the QT/RR slope, which is the slope of the QT plotted against the preceding RR interval (time between two QRS peaks) has been attracting interest, and has been investigated by three groups as a risk predictor. After finding that patients with inducible ventricular tachycardia had greater QT/RR slope [Extramiana 1999a], the group led by P. Coumel and P. Maison-Blanche studied QT/RR slope in the EMIAT database (European Myocardial Infarction Amiodarone Trial). In this trial, patients were followed for a mean of 21 months. Ambulatory electrocardiographs, usually referred to as Holter monitors after their inventor, Dr. Norman J. Holter, are portable devices for continuously monitoring the electrical activity of the heart for extended periods, the standard duration of which is 24 hours, and in circumstances that are not replicable in the laboratory. Its extended recording period is sometimes useful for observing occasional cardiac arrhythmias that would be difficult to identify in a shorter period of time. Comparison of Holter (24 hour) electrocardiographic records from 118 cardiac death patients and 118 matched survivors showed that patients who died from SCD had a steeper QT/RR slope in the 2 hours around the morning heart rate acceleration period than patients who died non-sudden deaths [Milliez 2005]. QT/RR slope was the only independent predictor of whether a cardiac death was sudden or non-sudden in a multivariate model that included no electrocardiographic predictors, except for number of ventricular premature complexes and heart rate. Another group studied QT/RR slope using a different calculation technique in the GREPI database (Groupe d'Etude du Pronostic de l'Infarctus du Myocarde). They used 265 Holter records from recent infarction patients, who were followed for a mean of 81 months. Of electrocardiographic predictors, steep daytime (9 AM-9 PM) QT/RR slope was found to be the strongest predictor of SCD followed by night time heart rate and the SDANN (Standard Deviation of Average Normal RR intervals) measure of heart rate variability [Chevalier 2003]. In contrast to these two post-infarction studies, Smetana et al studied QT/RR slope in 866 Holter records from the same EMIAT database as the Coumel Maison-Blanche group, but using a different technique for QT/RR slope calculation and different statistical design, and reached the completely opposite conclusion that flatter, rather than steeper QT/RR slope predicted SCD [Smetana 2004]. These studies suggest that QT/RR slope calculation methods need to be grouped according to scientifically grounded criteria, then compared in the same cohort of patients. These studies have also failed to assess independence of QT/RR slope as a predictor of SCD in multivariate analyses that include newer, more potent electrocardiographic predictors of cardiac mortality and SCD, such as heart rate turbulence [reviewed in Watanabe 2004] and deceleration capacity [Bauer 2006a].

The presence of hysteresis between heart rate change and corresponding QT change is a significant difficulty that arises when one tries to compute QT/RR slope. In the field of cardiac function research, the expression hysteresis is used to denote two types of hysteresis, a first type that refers to the variable relatively short timescale lag between changes in RR and corresponding changes in QT (generally measurable in seconds or minutes), and a second type which refers to the relatively long timescale lag (generally measurable in hours) between RR and QT that is related to circadian variations in autonomic tone. To preclude uncertainties related to distinguishing between these two forms of hysteresis, the expression hysteresis$_{VAR}$ will be utilized herein to denote the short term RR change instigated type of hysteresis, and the expression hysteresis$_{CIRC}$ will be utilized herein to denote the longer term circadian related hysteresis. Describing hysteresis$_{VAR}$ first: after an abrupt change in heart rate, QT takes time to attain its new value [Arnold 1982, Lau 1988]. For example, if heart rate were to change rapidly from 60 bpm to 100 bpm, QT during the first minute at 100 bpm would be greater than QT that had been given time to shorten to a steady state value. Likewise, if heart rate were suddenly switched back to 60 bpm, the QT during the first minute back at 60 bpm would be shorter than QT that had been given time to lengthen to the steady state value at 60 bpm. This temporal lag causes QT to be different at identical heart rates, depending on whether you are measuring a transient value, or the steady state value. This phenomenon is called QT hysteresis in the literature, and can be quantified as the difference between QT values at a pre-determined heart rate [Lewis 2006]. The presence of such hysteresis$_{VAR}$ produces a cloud of points when QT is plotted against RR, because there isn't a single QT value for a given RR, and hysteresis$_{VAR}$ reduces both the slope value and the r squared value of the regression. Describing hysteresis$_{CIRC}$ next: multiple studies have shown that QT is greater at night than during the daytime at the same heart rate [Browne 1983a, Bexton 1986, Cinca 1986, Murakawa 1992, Anselme 1996, Badilini 1999]. This is attributed to the predominance of vagal autonomic nerve activity at night. Murakawa et al specifically correlated the day-night difference in QT interval with the day-night difference in the HF to HF+LF power ratio of the heart rate variability parameters HF (high frequency) and LF (low frequency) power. Pharmacological studies of the autonomic contribution to QT agree that atropine reduces QT, while propranol and isoproterenol produce no changes [Ahnve 1982, Browne 1983b, LeCocq 1989, Cappato 1991]. Studies contrasting exercise and artificial pacing have shown that QT shortening in exercise is greater than that produced by heart rate increase alone, a difference attributed to changes in autonomic tone [Rickards 1981, Davey 1999]. Finally, two studies using heart transplant patients found that transplanted (anatomically denervated) hearts displayed blunted or absent day-night difference in QT [Bexton 1986, Alexopoulos 1988]. Alexopoulos et al also noted that transplanted hearts had shorter QT over 24 hour periods and during sleep, compared to control, but not during wake periods. To summarize autonomically induced hysteresis$_{CIRC}$ in man, studies in man largely agree in suggesting that QT is prolonged by vagal activation, and that some QT shortening is produced by circulating catecholamines.

The presence of heart rate change induced hysteresis$_{VAR}$ and autonomically induced hysteresis$_{CIRC}$ both complicate QT/RR slope measurement. In trying to deal with the problem of measuring variable slope caused by circadian hysteresis$_{CIRC}$, some investigators have chosen to measure QT/RR slope separately for day vs. night. These studies are in agreement that QT/RR slope is greater during the day than at night [Coumel 1995, Anselme 1996, Extramiana 1999b]. To deal with hysteresis$_{VAR}$, some investigators analyze only the portions of the QT/RR plot where heart rate has not changed for several minutes [Badilini 1998, Aytemir 1999]. There have also been attempts to quantify hysteresis$_{VAR}$ using computationally sophisticated techniques. One method computes the lag time between RR and QT change and effectively measures the slope after the QT has been shifted by that lag time [Neilson 2000, Lang 2001]. To use a crude example, if QT takes 3 seconds to adjust to a new heart rate of 100 bpm, one plots the QT 3 seconds after the heart rate change against the 100 bpm heart rate, instead of all the QT values traversed while adjusting to the new heart rate. The other method produces two values to characterize the temporal adaptation of QT to changes in heart rate, Lag, which describes time in seconds that RR intervals influence later QT values (140 sec on average, range 2-215 sec), and Lambda, a time constant of QT adaptation (average 48+/−8 beats) [Pueyo 2003].

In contrast to these many studies by clinician scientists who have been studying the relation between QT interval and SCD over many decades spurred by clinical experience, basic scientists have only over the last decade or so begun to show experimentally and theoretically, that the slope of action potential duration plotted against heart rate is closely coupled to arrhythmogenesis [Chialvo 1990, Watanabe 1995, Riccio 1999, Garfinkel 2000]. Action potential duration is the in vitro surrogate of the QT interval, and the term repolarization can be employed to refer to both QT interval and action potential duration. Nevertheless, basic scientists have produced many insights and predictions that could advance the field of repolarization parameter based SCD risk prediction. However, despite the clinical progress that might be made applying such knowledge, focused attempts to reconcile clinical data and specific experimental and theoretical results in a 1:1 fashion by scientists on either side of the clinical/basic scientist divide are thus far lacking. Articles in publications on the two sides of the divide generally lack even citations to studies by the other side, much less collaborative efforts. For instance, Holter ECG data in man (i.e. clinically oriented data compilation) is rarely collected to match experimental conditions (which would be considered to be standard procedure from a basic scientist perspective). A typical patient eats, sleeps, moves, takes medications, has various co-morbidities, and their heart rate changes to account for metabolic needs. In animal experiments, repolarization related data is measured with carefully planned stimulation protocols that absolutely control heart rate, with rare exceptions [Lux 2003]. Nevertheless, the inability of previous QT studies to produce definitive risk predictors with large hazard ratios suggest that interdisciplinary research and dialogue is necessary. It is perhaps telling that the best known and successful application of basic science knowledge to non-invasive risk prediction in recent years has been the use of T wave alternans to predict arrhythmia susceptibility. Perhaps this exception to the prevailing rule is because Dr. David Rosenbaum, a key investigator in this field, has been conducting both of the clinical and basic science studies necessary to realize the potential of the basic science findings.

In animals, Dr. Peng-Sheng Chen's group recently succeeded in recording autonomic nerve activity directly from sympathetic and vagal nerves using telemetry in conscious dogs, before and after heart failure induction by pacing. In their study, they found that integrated sympathetic nerve activity, though not vagal activity, showed significant circadian variations using cosinor analysis [Ogawa 2007]. These results give further support to the hypothesis that hysteresis-$_{CIRC}$ of QT is caused by circadian variations in autonomic tone. In the past, before Dr. Chen's recent success with direct autonomic nerve recordings, demonstration of the effects of autonomic tone on QT relied on interpreting the effects that stimulating or cutting autonomic nerves had on repolarization properties in animal models. Two early studies found left sided sympathetic nerve stimulation to increase QT interval [Yanowitz 1966, Schwartz 1975], whereas two later studies found that effective refractory period, a surrogate measure of QT, decreased [Martins 1980, Inoue 1987]. Use of different anesthetics in these studies were suggested as a possible reason for the contradictory findings [Zaza 1991]. However, Opthof et al who used ventricular fibrillation interval as an index of local refractoriness, found that although the most common response to stellate ganglion stimulation was shortening of the ventricular fibrillation interval, some sites showed prolongation, the response was variable from dog to dog, depended on location in the ventricle, and whether the left or right stellate ganglion was stimulated [Opthof 1991]. In other words, just as left/right dominance of coronary arteries varies from individual to individual, Opthofs results suggested that there was no universal pattern of innervation of the ventricles by the left or right sided sympathetic nerves.

However, the inconsistent results of sympathetic stimulation on QT values could again indicate the nonlinear heart rate dependence of measures of repolarization (including QT interval, effective refractory period, or ventricular fibrillation interval) that present difficulties in interpreting animal study results. This property makes it difficult to 'compare' and conclude whether autonomic stimulation or removal has altered repolarization duration without fixing the heart rate. All of the studies cited above controlled heart rate by pacing, or in the case of the Inoue study, by titration of sympathetic and vagal stimulation to achieve the same heart rate. Zaza et al [1991] tried to circumvent this problem by fitting the action potential duration vs RR interval relationship to a hyperbolic function. Their results (see their FIG. 4) show the left and bilateral stellectomy curves intersecting the control curve, and thereby give visual proof that left stellectomy decreases action potential duration at short RR intervals, increases it at long RR intervals, and doesn't change it at the RR interval at which the curves intersect. In other words, the study of Zaza et al demonstrates that although fixing heart rate is better than comparing repolarization measures at different heart rates, it still fails to give the whole story. The intersecting curves may explain the contradictory results of left stellectomy effect on QT interval by different researchers, better than arguments about the kind of anesthetic that was used. So again, the Zaza results emphasize the importance of analyzing the QT/RR interval relationship as a whole, such as by Lissajous analysis, rather than for a proscribed segment.

Given the extreme negative consequences (unnecessary SCD) of errors in underutilizing defibrillator implantation, as well as the massive costs (unnecessary surgical risk, discomfort, and wasted billions of dollars in medical expenditures) incurred with the present treatment protocol, it is abundantly evident that improved means to accurately forecast risk of SCD are desirable.

SUMMARY OF THE INVENTION

Embodiments of the present invention provide systems and methods of discerning assessments of risk of SCD from heart function electrocardiograph records by using Lissajous analysis, among other factors. Initially, information of the patient's heart function is garnered via a Holter monitor continuously recording electrocardiograph measurements, generally over a 24 hour period. As described in the background of the invention, these extended electrocardiograph records are often noisy in short term (from fractions of seconds to minutes) detail, inconsistent in manners of variation between individuals, and subject to longer term variations (from substantial fractions of to multiples of hours), both in type and magnitude, over different times of the day. One principal objective of the present invention is to provide a means to process the raw Holter electrocardiograph record to accommodate individual patients' variations in autonomic tone so that a general approach can discern relative SCD risk among a population of patients that are candidates for implanted defibrillators. Among the key aspects of the present invention are a multipart approach that utilizes elements of the Holter electrocardiograph record itself to effect the discerning of relative SCD risk. A crucial result of the present invention will be the establishment of a QT/RR interval slope magnitude that indicates a patient's relative risk of at least one of SCD, SCD associated cardiac function attributes, ancillary deleterious cardiac conditions, and cardiac function attributes associated with these ancillary deleterious cardiac conditions. Members of this group, both individually and collectively, of undesirable cardiac related issues will be referred to herein, for purposes of economy of expression only, as cardiac adversities. Provision of the capability of stratifying risk of at least one cardiac adversity in correspondence with the present invention's establishment of the QT/RR interval slope magnitude is a vital benefit of the present invention. An accurate and reliable risk stratification could enable better targeting that will increase the cost-effective deployment of medical resources, as well as ensuring that the access to medical resources is available to those that are more likely to need them, in addition to mitigation of at least some of the shortcomings of the current approaches detailed in the preceding background to the invention.

A number of embodiments of the present invention provide general approaches for establishing a Lissajous slope utilizable similarly to the currently utilized QT/RR interval slope, but that unlike existing approaches, do not require subjective or patient-specific adjustments to deal with the hysteresis$_{VAR}$ that exists between RR and QT interval change. Embodiments of the present invention have no need to define a range of RR over which to calculate QT/RR slope, or to decide which hours of the 24 hour plot to use for comparisons with other patients, as do the current approaches. Many methods according to the present invention involve fitting cosine functions to the 24 hour fluctuations of RR and QT interval, using, among other techniques, regression analysis, and determining a "Lissajous slope", which can be roughly thought of as somewhat comparable to a 24 hour average of what is conventionally referred to as the QT/RR interval slope. The mechanism of hysteresis$_{CIRC}$ between RR and QT over the day, and how heart failure affects hysteresis$_{CIRC}$, needs to be better understood, as illustrated by the concurrence of the QT/RR interval slope (conventionally determined) varying in steepness according to the time of day, and the incidence of SCD clustering in the morning hours. It is known that RR and QT are determined by the relative magnitudes of the sympathetic and vagal nerve inputs to the heart, but the only way to determine whether a particular decrease in RR is due to an increase in sympathetic activity or a decrease in vagal activity is by recording nerve activity directly, which is not feasible as a standard diagnosis protocol for people. Accordingly, the present invention can provide means of accounting for uncertainties about individual differences in autonomic tone without necessitating invasive and impractical measures of the individual's actual nerve activity; and additional information that can be used to accomplish some of the treatment objectives for cardiac adversities, including determining, at least partially, whether certain issues are likely due primarily to autonomic tone effects, or other factors. The present invention can also be utilized to expand knowledge of, and potentially improved use of, other measures of cardiac adversities, such as heart rate variability, by providing independent measures that can corroborate, contradict, or otherwise further inform judgments of these other measures' utility and their individual findings.

In general, the approaches effected by several embodiments of the present invention involve procedures capable of establishing a stratification of risk of at least one cardiac adversity by accessing an extended period of electrocardiograph recordings; determining RR and QT acrophases from within the extended periods and a phase difference $\phi$ between their respective times of occurrence; discerning the QT and RR values from the extended period electrocardiograph record and (optionally) partitioning and (optionally) averaging these partitioned QT and RR values; fitting (with regression analysis techniques) formulas for a resulting $RR_{FIT}$ and $QT_{FIT}$ to the RR and QT values (raw, partitioned, averaged, or combinations thereof); determining a Cr and a Cq coefficients from the $RR_{FIT}$ and $QT_{FIT}$ formulas, respectively, and (optionally) using the Cr and Cq coefficients, as well as $\phi$, to determine a Lissajous slope; plotting (optionally) a representation of the extended period of $RR_{FIT}$ and $QT_{FIT}$ values to produce a RR-QT Lissajous slope curve and (optionally) analyzing at least one feature of the plotted representation; and realizing at least one stratification of risk of at least one cardiac adversity based on at least one correlation between said at least one cardiac adversity risk and at least one of the parameters established in the above procedures.

Other objects and features will be in part apparent and in part pointed out hereinafter.

DETAILED DESCRIPTION OF THE PREFERRED EMBODIMENTS

Figure 1:
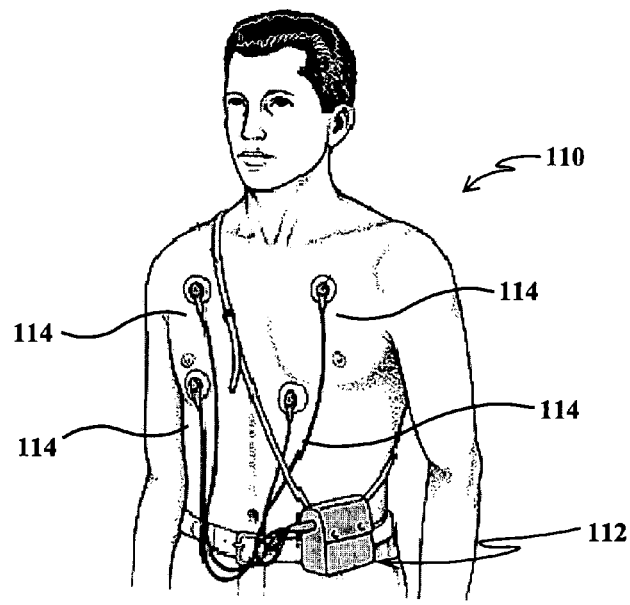
FIG. 1 depicts a view of a patient wearing a Holter monitor in a typical ambulatory configuration for registering an extended period of electrocardiograph recordings.

In the following description, identical numbers indicate identical elements. Where an element has been described in one Figure, and is unaltered in detail or relation in any other Figure, said element description applies to all Figures.

A detailed explication of a general procedure common to many of the approaches employed by various embodiments of the present invention will generally involve establishing stratification of at least one risk of a cardiac adversity by:
 a) Accessing at least one 24 hour (generally) period of a patient's electrocardiograph recordings;
 b) Ascertaining both an RR and a QT acrophase (time of peak value=$-\phi_R$ and $-\phi_Q$, respectively) from that patient's 24 hour electrocardiograph record utilizing regression analysis;
 c) Determining a phase difference $\phi$ equal to the difference between the RR and QT acrophases;
 d) Discerning 24 hour records of the QT and RR values from the patient's electrocardiograph recordings;
 e) (Optionally) Partitioning each of these 24 hour RR and QT value records into bins that encompass a selected period of time, such as 30 minutes apiece, and finding an average RR or QT value, respectively, for each of the bins;
 f) Fitting (with regression analysis) the 24 hour RR and QT (raw or partitioned) records to the formulas:

$$RR_{FIT}=RR_{MEAN}+Cr \cos [(2\pi/24)(t+\phi_R)] \text{ and}$$

$QT_{FIT}=QT_{MEAN}+Cq \cos [(2\pi/24)(t+\phi_Q)]$, wherein $RR_{MEAN}$ is the mean RR value and $QT_{MEAN}$ is the mean QT value for the 24 hour period, and further wherein "t" is a variable indicating the time of the respective RR or QT values, while Cr and Cq are defined as the RR and QT circadian amplitude coefficients, respectively;
 g) Determining the Cr and Cq values that result from the above fitting of the formulas to the 24 hour RR and QT records, and (optionally) determining a:

$$\text{Lissajous slope}=(Cq/Cr)\cos [(2\pi/24)(\phi_R-\phi_Q)];$$

h) (Optionally) Plotting $RR_{FIT}$ vs. $QT_{FIT}$ to produce a RR-QT Lissajous curve representation of the 24 hour electrocardiograph record, and optionally further determining at least one feature, such as the area encompassed by the RR-QT Lissajous curve, of the plotted representation; and
 i) Realizing at least one stratification of risk of at least one cardiac adversity by identifying at least one correlation between said stratification of risk and at least one of said Lissajous slope, said plotted representation feature, at least one of said $RR_{FIT}$ and said $QT_{FIT}$, and combinations thereof.

In the above description of a general procedure common to many of the approaches employed by various embodiments of the present invention, it should be understood that the detailed aspects of the description are focused on certain specific attributes of a particular application of the procedure, for purposes of clarity of illustration only. Included among the aspects of the procedure that can be varied, and still fall within the scope of the present invention, are that the specific quantities being measured and analyzed can differ from the RR and QT intervals specified herein, as well as the period of periodic rhythm differing from 24 hours, in which case the factor of 24 in the equations of f) and g) will need to be replaced with the period of the periodic rhythm being studied. Additional utilities of the present invention include, but are not limited to, employing at least one of said RR or QT acrophases, $\phi$, $RR_{FIT}$, $QT_{FIT}$, Cr, Cq, Lissajous slope, RR-QT Lissajous curve, plotted representation feature, and combinations thereof to effect at least one of risk stratification for at least one cardiac adversity, risk stratification for at least one non-cardiac health issue, risk stratification for at least one condition that can affect a cardiac adversity, and indications of at least one collateral issue that can influence biologically related research investigations. An example of such a collateral issue would be, due to the influence of the patient's autonomic tone on the phase difference $\phi$, an indication that when a particular determined $\phi$ is found that that may suggest a potentially deleterious condition which affects that patient's autonomic tone, so that the collateral issue would be the condition of that patient's systems which influence their autonomic tone.

As shown in FIG. 1, a patient 110 is wearing a typical Holter monitor arrangement involving a base electrocardiograph 112 that receives, processes, and plots the heart function information of the patient 110 that is sensed by the electrodes 114.

Figure 2:
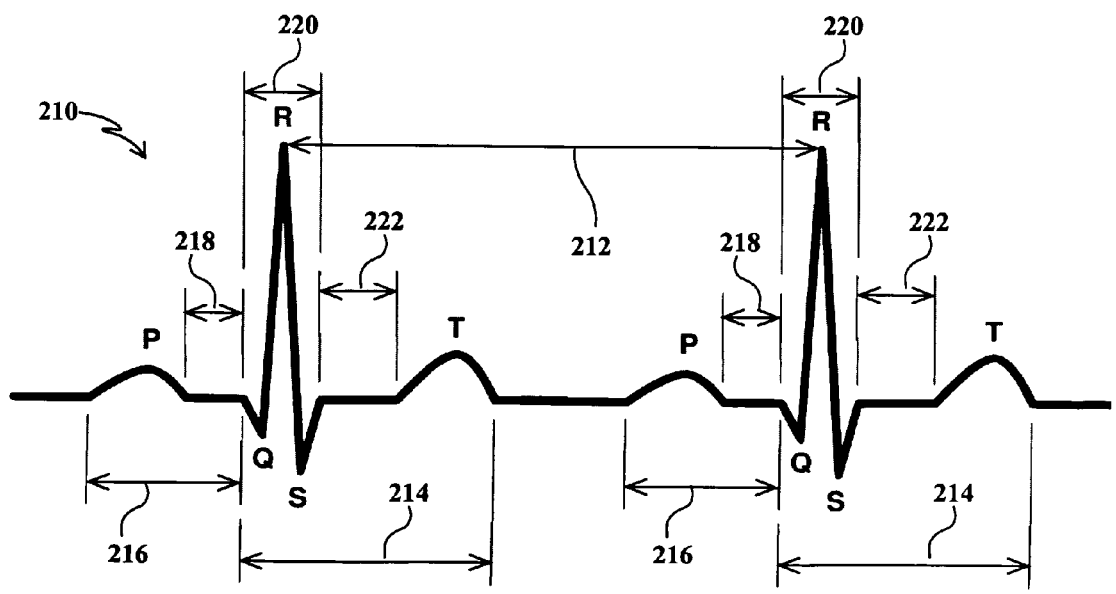
FIG. 2 depicts a representative illustration of a pair of heartbeats as recorded by an electrocardiograph.

FIG. 2 shows an illustrative representation 210 of a pair of heartbeat recordings such as would be registered by an electrocardiograph 112. The dominant characteristic features of the heartbeat plots are termed P, Q, R, S, and T. The intervals and sections of the electrocardiograph heartbeat plots shown in the illustrative representation 210 are the RR interval 212, the QT interval 214, the PR interval 216, the PR segment 218, the QRS complex 220, and the ST segment 222.

Figure 3:
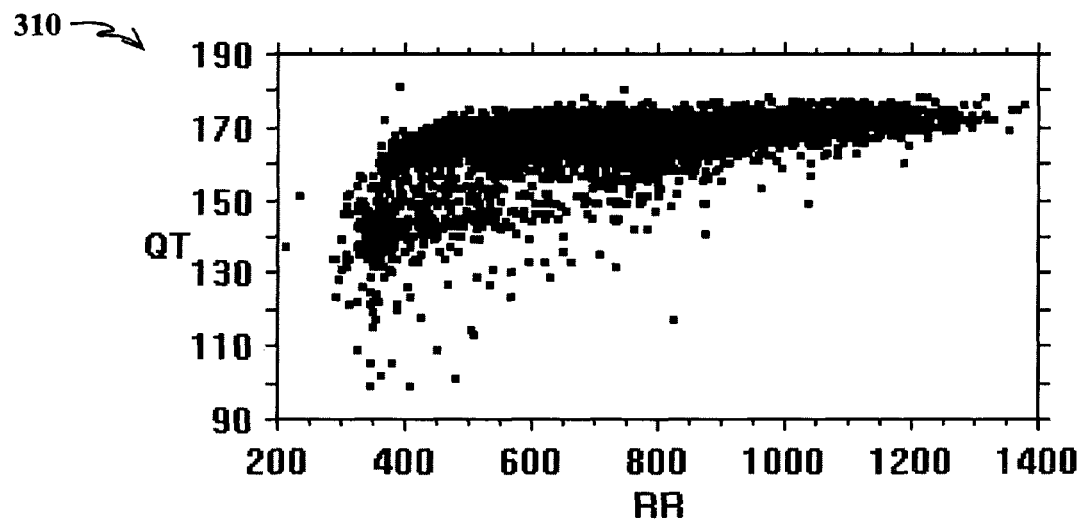
FIG. 3 depicts a plot of raw QT vs. RR intervals for an hour's worth of canine ECG data.

FIG. 3 illustrates the "noisiness" of the raw data from an electrocardiograph by depicting a plot 310 of QT vs. RR interval for an hour's worth of canine ECG data. The numerals on the axes denote milliseconds, and though, of course, canines are not humans there are sufficient similarities for the studies of canines to be substantially useful as an animal model for investigating humans, particularly in situations such as cardiac health issues wherein the consequences can be dire, and because some of the best information available in autonomic tone studies also involves canine study subjects, it is clear that data garnered from studies of canines is revelatory of performance in humans. In any case, FIG. 3 is presented herein purely for purposes of contrast to demonstrate the issues that are still not yet satisfactorily handled by the current approaches, i.e. to show the lack of clarity available hereto now, due probably in large part to $hysteresis_{VAR}$, which is unmistakably apparent in FIG. 3.

Figure 4:
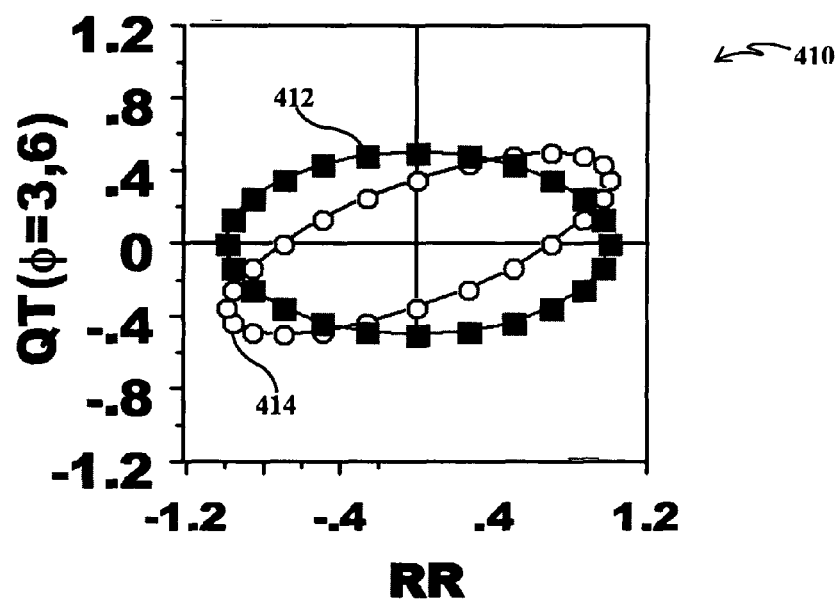
FIG. 4 depicts a pair of plot representations of characteristic Lissajous slope curves for 2 examples of $\phi$.

FIG. 4 shows a plot 410 of a pair of Lissajous curves according to the present invention, with each of the curves being formed from 24 hourly points (the curves are hypothetical, not measured because each individual patient's plot will not produce an illustration of the overall phenomena and its variations with sufficient clarity). The curve 412 is produced by a $\phi$ of 6 hours, while the curve 414 is produced by a $\phi$ of 3 hours. As $\phi$ is varied larger in magnitude past 6 hours the ellipse will change further in shape so that it will appear more and more like a mirror image of curve 412. For a $\phi$ of 0 or 12 hours, the resulting Lissajous curve plot would be a line, with the slope being positive for a $\phi$ of 0 and negative for a $\phi$ of 12 hours. In clinical application, $\phi$, the $RR_{FIT}$'s and $QT_{FIT}$'s, Cr and Cq, and the various other factors will be at least partially indicative of patient specific parameters, and hence will vary individually. The factors that induce the individual variations are hence indicative of individually variable attributes of the patient's condition, which in turn provides the present invention with the individually variable results from the present invention's novel approaches that will produce the more accurately individually responsive risk assessments.

The method embodiments of the present invention employ a variety of the various steps described previously, as well as certain well known to those of skill in the art (heart condition diagnosis, treatment, and research) auxiliary steps which would be expected to be generally concomitant procedures when at least one of the embodiments of the present invention are being utilized. These concomitant procedures can include, but are not limited to, drug treatment protocols, health and wellness actions and ingestibles and injectibles, and related treatments that are intended to more clearly enable the present invention's resolution of the patient's degree of risk. As a system, the various aspects will fulfill the functions explicated in a) through i) with various parts such as a discerner that will effect d) detailed previously. It is well known to many in the art of medical equipment design and production, as well as those versed in the fields of electrical engineering and software design, that carrying out the steps and functions explicated herein are relatively easily accomplished with presently available equipment and software (such as a modern laptop with standard operating system and average relevant software), much less the also easily understood and executed procedures and approaches implementable to design and/or develop specialized hardware and/or software. The actual development and design of this equipment is not the focus of the present invention, and hence is not explicate in exhaustive depth herein.

In a representative diagnosis and treatment procedure, once a patient has undergone the extended period of electrocardiograph recording of their heart function, and the various factors and determinations needed to assess their cardiac adversity risk with the above described procedures have been executed, the present invention's risk stratification can be effected. At least one of the Lissajous slope by itself, and the Lissajous slope in combination with other independent risk stratifiers, such as left ventricular ejection fraction, are combined to construct a risk score. The score, for example, can be constructed from weighted points for each abnormal parameter, such as +2 for ejection fraction <30%, +1 for ejection fraction 30-50%, and 0 for ejection fraction >50%; along with +1 for Lissajous slope>threshold criteria, 0 for Lissajous slope<threshold criteria; +1 for positive T wave alternans test, 0 for negative; and +2 for QRS duration>0.14 sec, +1 for QRS duration 0.12-0.14 sec, 0 for normal QRS duration. The scores are summed for each patient, and when the sum score is greater than a specified value, say 3, the patient is then deemed at high risk for a cardiac adversity and will receive a defibrillator, or other aggressive medical treatment, such as constant telemetric monitoring.

In view of the above, it will be seen that the various objects and features of the invention are achieved and other advantageous results obtained. The examples contained herein are merely illustrative and are not intended in a limiting sense.

What is claimed is:

1. A method of stratifying risks of an adverse cardiac event comprising the steps of:

ascertaining, from a first duration of electrocardiographic records, RR and QT interval data;

determining mean RR and QT interval data, denoted by $RR_{MEAN}$ and $QT_{MEAN}$, respectively;

fitting, with a calculator, at least a portion of at least one of the RR and QT interval data to at least one of first and second formulas that include fitting related measures and define $RR_{FIT}$ and $QT_{FIT}$, respectively, said first formula being, $$RR_{fit} = RR_{mean} + Cr \cos[(2\pi/24)(t+\phi_R)],$$

and said second formula being, $$QT_{fit} = QT_{mean} + Cq \cos[(2\pi/24)(t+\phi_Q)],$$

wherein t represents a temporal measure and said fitting at least partially establishes the fitting related measures Cr, Cq, $\phi_R$, and $\phi_Q$, said Cr and Cq denoting RR and QT circadian amplitude coefficients, respectively, and said $\phi_R$ and $\phi_Q$ denoting RR and QT acrophases, respectively;

establishing at least a first correlation between at least a first cardiac adversity relative risk related attribute and at least one of the fitting related measures; and stratifying relative risk of at least a first cardiac adversity in response to the at least a first correlation, said stratifying involving at least a first stratifying mathematical expression, said first stratifying mathematical expression involving at least two of the fitting related measures.

2. A method of stratifying risks of an adverse cardiac event according to claim 1, wherein said at least two fitting related measures are selected from a group consisting of said Cr, Cq, $\phi_R$, $\phi_Q$, $RR_{FIT}$, and $QT_{FIT}$.

3. A method of stratifying risks of an adverse cardiac event according to claim 1, wherein the first stratifying mathematical expression determines a Lissajous slope $\Delta_{LJ}$ from a third formula, $$\Delta_{LJ} = (Cq/Cr) \cos[(2\pi/24)(\phi_R - \phi_Q)].$$

4. A method of stratifying risks of an adverse cardiac event according to claim 1, wherein the first stratifying mathematical expression determines a phase difference $\phi$ from a fourth formula, $$\phi = \phi_R - \phi_Q.$$

5. A method of stratifying risks of an adverse cardiac event according to claim 1, said fitting involving varying at least one of said Cr and Cq.

6. A method of stratifying risks of an adverse cardiac event according to claim 1, said fitting at least partially involving regression analysis.

7. A method of stratifying risks of an adverse cardiac event according to claim 1, further comprising the step of plotting said $RR_{fit}$ in relation to said $QT_{fit}$ to produce a RR-QT Lissajous curve representation of at least a portion of the first duration of electrocardiograph records and resolving at least a first Lissajous curve representation feature, denoted by $F_{LjC}$, of the plotted representation, wherein said resolving the $F_{LjC}$ entails said at least two fitting related measures.

8. A method of stratifying risks of an adverse cardiac event according to claim 1, further comprising the step of distinguishing at least a first treatment in response to said relative risk stratifying, said first treatment involving either or both of at least partially mitigating or at least partially inhibiting occurrence of said adverse cardiac event.

9. A method of stratifying risks of an adverse cardiac event according to claim 1, further comprising the step of engendering implementation of at least a first treatment in response to said relative risk stratifying, said first treatment involving either or both of at least partially mitigating or at least partially inhibiting occurrence of said adverse cardiac event.

10. A method of stratifying risks of an adverse cardiac event according to claim 1, wherein a measure of the goodness of fit of at least one of the first and second formulas to at least one of the fitted portions of the RR and QT interval data is employable as at least one the fitting related measures.

11. A system for stratifying risks of an adverse cardiac event comprising:

a data assayer for discerning RR and QT interval data including mean RR and QT interval data, denoted by $RR_{MEAN}$ and $QT_{MEAN}$, respectively, wherein the assayer realizes said discerning from a first duration of received electrocardiograph recordings;

a calculator for fitting at least a portion of at least one of the RR and QT interval data, said fitting involving at least one of first and second formulas, wherein the first and second formulas include fitting related measures and define quantities $RR_{FIT}$ and $QT_{FIT}$, respectively, said first formula being, $$RR_{fit} = RR_{mean} + Cr \cos[(2\pi/24)(t+\phi_R)],$$

and said second formula being, $$QT_{fit} = QT_{mean} + Cq \cos[(2\pi/24)(t+\phi_Q)],$$

wherein t represents a temporal measure and said fitting at least partially establishes the fitting related measures Cr, Cq, $\phi_R$, and $\phi_Q$, said Cr and Cq denoting RR and QT circadian amplitude coefficients, respectively, and said $\phi_R$ and $\phi_Q$ denoting RR and QT acrophases, respectively, said calculator further establishing at least a first correlation between at least a first cardiac adversity relative risk related attribute and at least one of the fitting related measures; and a correlation responder able to stratify relative risk of at least a first cardiac adversity in response to the at least a first correlation, said stratifying involving at least a first stratifying mathematical expression, said first stratifying mathematical expression involving at least two of the fitting related measures.

12. A system for stratifying risks of an adverse cardiac event according to claim 11, further comprising a treatment distinguisher able to discriminate at least a first treatment in response to said relative risk stratifying, said first treatment involving either or both of at least partially mitigating or at least partially inhibiting occurrence of said adverse cardiac event.

13. A system for stratifying risks of an adverse cardiac event according to claim 11, further comprising a treatment implementer able to engender at least a first treatment in response to said relative risk stratifying, said first treatment involving either or both of at least partially mitigating or at least partially inhibiting occurrence of said adverse cardiac event.

* * * * *